US00PP28205P2

(12) United States Plant Patent
O'Neill

(10) Patent No.: US PP28,205 P2
(45) Date of Patent: Jul. 18, 2017

(54) ***BOUGAINVILLEA* PLANT NAMED 'VISTA3'**

(50) Latin Name: *Bougainvillea communis*
Varietal Denomination: Vista3

(71) Applicant: Jerome O'Neill, Juana Diaz, PR (US)

(72) Inventor: Jerome O'Neill, Juana Diaz, PR (US)

( * ) Notice: Subject to any disclaimer, the term of this patent is extended or adjusted under 35 U.S.C. 154(b) by 0 days.

(21) Appl. No.: 14/999,111

(22) Filed: Mar. 30, 2016

(51) Int. Cl.
*A01H 5/00* (2006.01)

(52) U.S. Cl.
USPC ..... Plt./256

(58) Field of Classification Search
USPC ..... Plt./256
See application file for complete search history.

*Primary Examiner* — Annette Para
(74) *Attorney, Agent, or Firm* — Cassandra Bright

(57) ABSTRACT

A new and distinct *Bougainvillea* cultivar named 'Vista3' is disclosed, characterized by yellow-orange bracts. Plants are very compact. The new variety is a *Bougainvillea*, typically produced as an ornamental plant.

1 Drawing Sheet

Latin name of the genus and species: *Bougainvillea communis.*

Variety denomination: 'Vista3'.

BACKGROUND OF THE INVENTION

The new cultivar is the product of chance discovery. The new variety originated as naturally occurring whole plant mutation of the unpatented variety *Bougainvillea communis* 'Juanita Hatten'. The inventor discovered the variety in a commercial planting of the parent variety in Juana Diaz, Puerto Rico in January of 2015.

After identifying the interesting flower color mutation, the inventor observed the single plant mutation for several months. First propagation was performed by terminal vegetative cuttings at a commercial greenhouse during February 2015, in Juana Diaz, Puerto Rico. Access to all plants was restricted, as plants were kept in a facility belonging to the inventor and not open to the public.

Through subsequent propagation by vegetative cuttings, multiple generations have been reproduced, which have shown that the unique features of this cultivar are stable and reproduced true to type.

SUMMARY OF THE INVENTION

The cultivar 'Vista3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Vista3'. These characteristics in combination distinguish 'Vista3' as a new and distinct *Bougainvillea* cultivar:

1. Very compact growth habit.
2. Color of mature bract is Yellow-Orange.
3. Abundant flowering, more flowers than typical of orange or yellow types.

PARENT COMPARISON

Plants of the new cultivar 'Vista3' are similar to the parent, in most horticultural characteristics. The new variety, however, produces bracts that are orange in color, whereas bracts of the parent variety are bright pink.

COMMERCIAL COMPARISON

Plants of 'Vista3' are similar in some horticultural characteristics to the variety *Bougainvillea* 'Orange King', unpatented. The new variety, however, differs in the following:

1. The new variety has Yellow-Orange bracts, the comparator has orange bracts with very strong pink coloration.
2. Plants of the new variety are more compact.

Plants of 'Vista3' are similar in most horticultural characteristics to the variety *Bougainvillea* 'Roseanka', unpatented. The new variety, however, differs in the following:

1. Many more inflorescence per plant than the comparator.
2. Bracts of the new variety are Yellow-Orange, bracts of the comparator are pink with orange and more salmon colored.
3. Plants of the new variety grow more vigorously.

BRIEF DESCRIPTION OF THE PHOTOGRAPH

The accompanying photograph in FIG. 1 illustrates in full color a typical plant of 'Vista3' grown outdoors at a commercial nusery in Juana Diaz, Puerto Rico. This plant is approximately 1 year old, shown planted in the ground. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'Vista3' plant. This plant was grown in a greenhouse in a commercial 6 inch pot, in Juana Diaz, Puerto Rico. The plant described is approximately 6 months old and consists of 3 rooted cuttings in 1 pot. Temperatures ranged from 15° C. at night and 18° C. to 24° C. during the day. No artificial light, photoperiodic treatments were given to the plants. Measurements and numerical values represent averages of typical plant types.

Botanical classification: *Bougainvillea communis* 'Vista3'.

PROPAGATION

Time to initiate roots: 14-21 days at approximately 25° C.

Root description: Roots are fine, fibrous and well branched.

Time to produce a rooted plant: Approximately 6 to 12 weeks.

Root color: Near Grey-Brown 199D and Greyed-Yellow 161D.

PLANT

Growth habit: This plant is an upright tender perennial, suitable for indoor ornamental use, or outdoor garden use in warm climates.

Pot size of plant described: 6 inch.

Height: 18 cm.

Plant spread: 23 cm.

Main stem color: Near RHS Brown N200C.

Main stem texture: Mainly smooth, minimal scaly texture.

Branching characteristics: Not free branching, moderate branching can be achieved with pinching.

Length of primary lateral branches: 6-10 cm.

Quantity of primary lateral branches: 2 per plant.

Characteristics of primary lateral branches:

*Diameter*.—Approximately. 0.3 to 0.4 cm.

*Color*.—Near RHS Grey 201B.

*Texture*.—Slightly rough, minimally scaly.

Internode length: 0.8 cm to 1.8 cm.

FOLIAGE

Leaf:

*Arrangement*.—Alternate, simple.

*Quantity*.—Approximately 6 per branch on a 6 month old plant.

*Average length*.—Average range about 3.5 cm to 7.5 cm.

*Average width*.—Average range about 2.5 cm to 3.9 cm.

*Shape of blade*.—Obovate.

*Apex*.—Mainly acute, some older leaves retuse.

*Base*.—Obtuse.

*Margin*.—Entire.

*Texture of top surface*.—Smooth.

*Texture of bottom surface*.—Smooth.

*Appearance of top surface*.—Matte.

*Appearance of bottom surface*.—Matte.

*Color*.—Young foliage upper side: Near RHS Green 137B. Young foliage under side: Near RHS Green 138A. Mature foliage upper side: Near RHS Green 137A. Mature foliage under side: Near RHS Green 137A.

*Venation*.—Type: Pinnate. Venation color upper side: RHS Yellow-Green 144B. Venation color under side: RHS Yellow-Green N144B.

*Petiole*.—Length: Average 1.0 cm to 3.2 cm. Diameter: 0.2 cm. Color: Near RHS Yellow-Green 144A. Texture: Smooth.

Other characteristics:

Thorns: One thorn occurs above a node. A thorn is not always present, sometimes no thorn above leaf or node. Thorn is pointed upwards; Young thorns are more flexible and less sharp. Old thorns are very sharp, strong and woody.

*Average thorn length*.—Mature thorn approximately 2.0 cm.

*Average thorn width at base*.—0.2 cm.

*Shape*.—Needlelike.

*Thorn curvature*.—None, straight.

*Thorn coloration*.—Young thorns near RHS Greyed-Orange 163B. Old thorns RHS Greyed-Green 197B.

FLOWER

Normal flowering period: Continuously from early Spring through Fall in Puerto Rico.

Inflorescence:

*Form*.—Axillary, compact cyme.

*Width of entire inflorescence*.—Average 8.0 cm.

*Height of entire inflorescence*.—Average 6.0 cm.

*Quantity of individual flowers in inflorescence*.—Avg. 3 on a 6 month old plant.

Flower longevity on plant: Approximately 10 days.

Quantity of inflorescence per plant: Avg. 4 to 8.

Quantity of bract clusters: Medium density. Average range 6 to 12 on a 6 month old plant.

Persistent or self-cleaning: Self-cleaning.

Bud:

*Shape*.—Oblanceolate.

*Length*.—0.4 cm.

*Diameter*.—0.3 cm.

*Color*.—Near RHS Yellow-Orange 16B.

Individual true flower:

*Form/type*.—Single, tubular flowers growing from the base of a single bract. The flowers have no petals or sepals. The individual true "flower" is small, and each cluster of three flowers is surrounded by three bracts. Sometimes the cluster consists of more flowers but the number of bracts is nearly always 3.

*Diameter*.—0.8 cm.

*Depth*.—0.25 cm.

*Days lasting on plant*.—Approximately one week.

Petals: No petals.

Bracts:

*Days lasting on plant*.—Approximately 10, self-cleaning.

*Type*.—Single.

*Shape*.—Ovate.

*Length*.—3.5 cm.

*Width*.—3.0 cm.

*Tip*.—Broadly acute.

*Base*.—Rounded.

*Margin*.—Entire.

*Aspect*.—Moderately undulating.

*Color*.—Under side of immature bract: RHS Yellow-Orange 21C. Upper side of immature bract: RHS Yellow-Orange 21C. Under side of mature bract: RHS Yellow-Orange 21D. Upper side of mature bract: RHS Yellow-Orange 21D. Bract vein color on under side: RHS Yellow-Green 144B. Bract vein color on upper side: RHS Yellow-Green 144C.

Sepals: No sepals observed.

Peduncles:

*Length*.—Average 3.8 cm.

*Diameter*.—0.2 cm.

*Angle*.—Approximately 45° to the lateral branch.

*Strength*.—Strong.

*Texture*.—Smooth.

*Color*.—Near RHS Yellow-Green 150C.

Pedicels:

*Arrangement*.—Individual flowers in whorls of 3, together on pedicels. Each individual flower sessile, implanted in a colorful bract.

*Length*.—2.0 cm.

*Diameter*.—0.1 cm.

*Angle*.—Average angle of 15 degrees.

*Strength*.—Moderately strong.

*Color*.—Near RHS Yellow-Green 145C.

Fragrance: None.

REPRODUCTIVE ORGANS

Stamens:

*Number*.—Average 8.

Anthers:

*Length*.—Approximately 0.05 cm.

*Color*.—Near Yellow-Orange 17D.

*Pollen*.—Color RHS Yellow-Orange 17C.

*Quantity*.—Scant.

Pistil:

*Number*.—1.

*Length*.—0.5 cm.

*Style*.—Length: 0.1 cm. Color: RHS Yellow-Green 145C.

*Stigma*.—Shape: Linear. Color: Near RHS Yellow Green 146C. Ovary Color: Near RHS Yellow Green 145B.

OTHER CHARACTERISTICS

Seeds and fruits: Seed production not observed.

Disease/pest resistance: Neither resistance nor susceptibility to diseases or pests has been observed in this variety.

Temperature tolerance: Tolerates high temperatures to at least 35 degrees Celsius. Frost is not tolerated. When roots are frozen completely, the plant will not recover.

Drought tolerance: No drought tolerance. Leaves and bracts will drop off the plant immediately under dry conditions.

What is claimed is:

1. A new and distinct cultivar of *Bougainvillea* plant named 'Vista3' as herein illustrated and described.

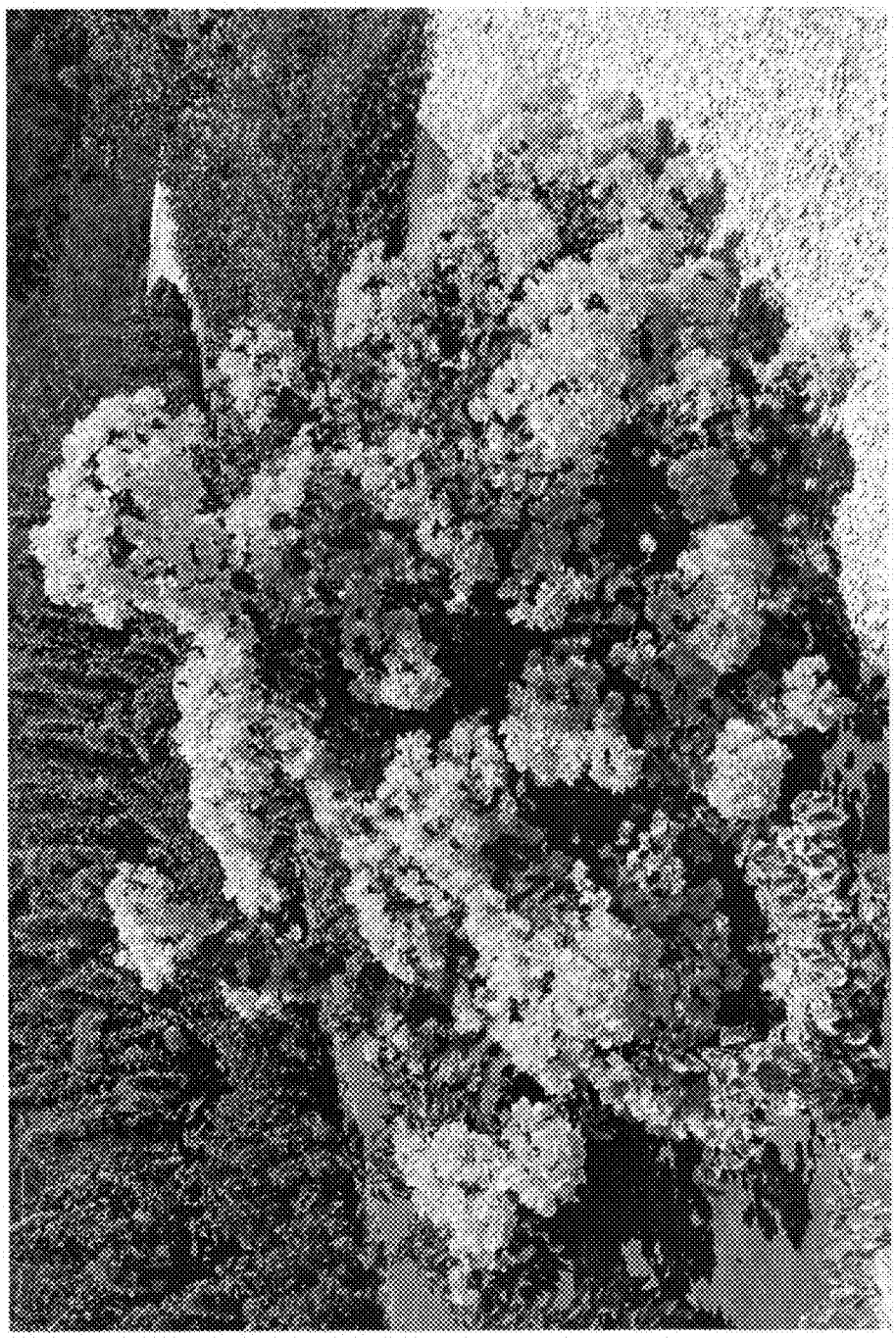

* * * * *